(12) United States Patent
Choi (10) Patent No.: US 6,575,942 B2
(45) Date of Patent: Jun. 10, 2003

(54) INJECTION NEEDLE UNIT FOR PORTABLE AUTOMATIC SYRINGE DEVICE

(76) Inventor: Soo Bong Choi, #5-908, Youwon Apt., 421-7 Yeonsoo-dong, Chungju-shi, Chungcheongbuk-do (KR)

( * ) Notice: Subject to any disclaimer, the term of this patent is extended or adjusted under 35 U.S.C. 154(b) by 67 days.

(21) Appl. No.: 10/003,657

(22) Filed: Oct. 23, 2001

(65) Prior Publication Data

US 2003/0009136 A1 Jan. 9, 2003

(30) Foreign Application Priority Data

Jul. 6, 2001 (KR) ......................................... 2001-40201

(51) Int. Cl.⁷ ................................................ A61M 5/00
(52) U.S. Cl. ............. 604/240; 604/164.02; 604/167.02; 604/535
(58) Field of Search ....................... 604/164.01, 164.02, 604/164.06, 164.08, 165.01, 165.02, 167.01–167.06, 533–535, 890.1, 93.01, 48, 19, 27, 502, 506, 507, 513

(56) References Cited

U.S. PATENT DOCUMENTS 4,417,889 A    11/1983   Choi ........................... 604/246
5,405,323 A  *  4/1995   Rogers et al. ............... 604/508

FOREIGN PATENT DOCUMENTS

EP    0298585 A1  *  1/1989   ............ A61M/5/28
JP    52-3292        1/1977

* cited by examiner

Primary Examiner—Brian L. Casler
Assistant Examiner—Lina T Kontos
(74) Attorney, Agent, or Firm—Sheridan Ross PC (57) ABSTRACT

Disclosed is an injection needle unit for a portable automatic syringe device adapted to perform an injection of liquid medicine into the body of a user for a prolonged time.

3 Claims, 12 Drawing Sheets

INJECTION NEEDLE UNIT FOR PORTABLE AUTOMATIC SYRINGE DEVICE

BACKGROUND OF THE INVENTION

1. Field of the Invention

The present invention relates to an injection needle unit for a portable automatic syringe device adapted to perform an injection of liquid medicine into the body of the user for a prolonged time, which includes a feeding tube, a connector coupled to an insulin pump included in the syringe device to connect the feeding tube to the insulin pump, and an injection needle member adapted to be penetrated into the abdomen of the user and connected to the insulin pump via the connector and feeding tube. More particularly, the present invention relates to an injection needle unit for a portable automatic syringe device which includes a feeding tube divided into first and second tube portions respectively connected to a syringe pump connector and an injection needle member, first and second head units respectively coupled to facing ends of the first and second tube portions, and a coupling ring for separably coupling the first and second head units to each other, thereby being capable of achieving easy separation and coupling of the injection needle member from a syringe pump.

2. Description of the Prior Art

Figure 1:
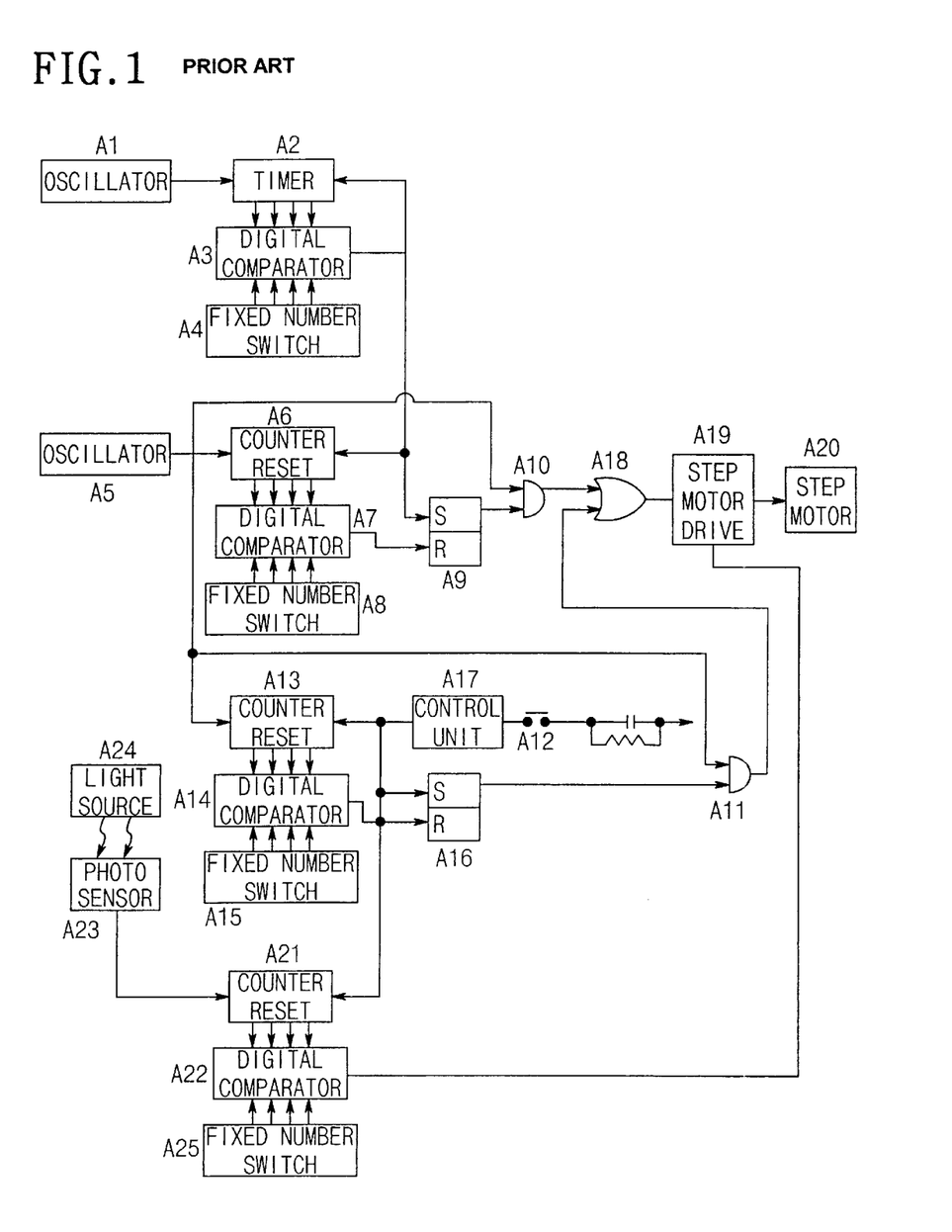
FIG. 1 is a block diagram illustrating a control circuit used in a conventional automatic syringe device.
Figure 2:
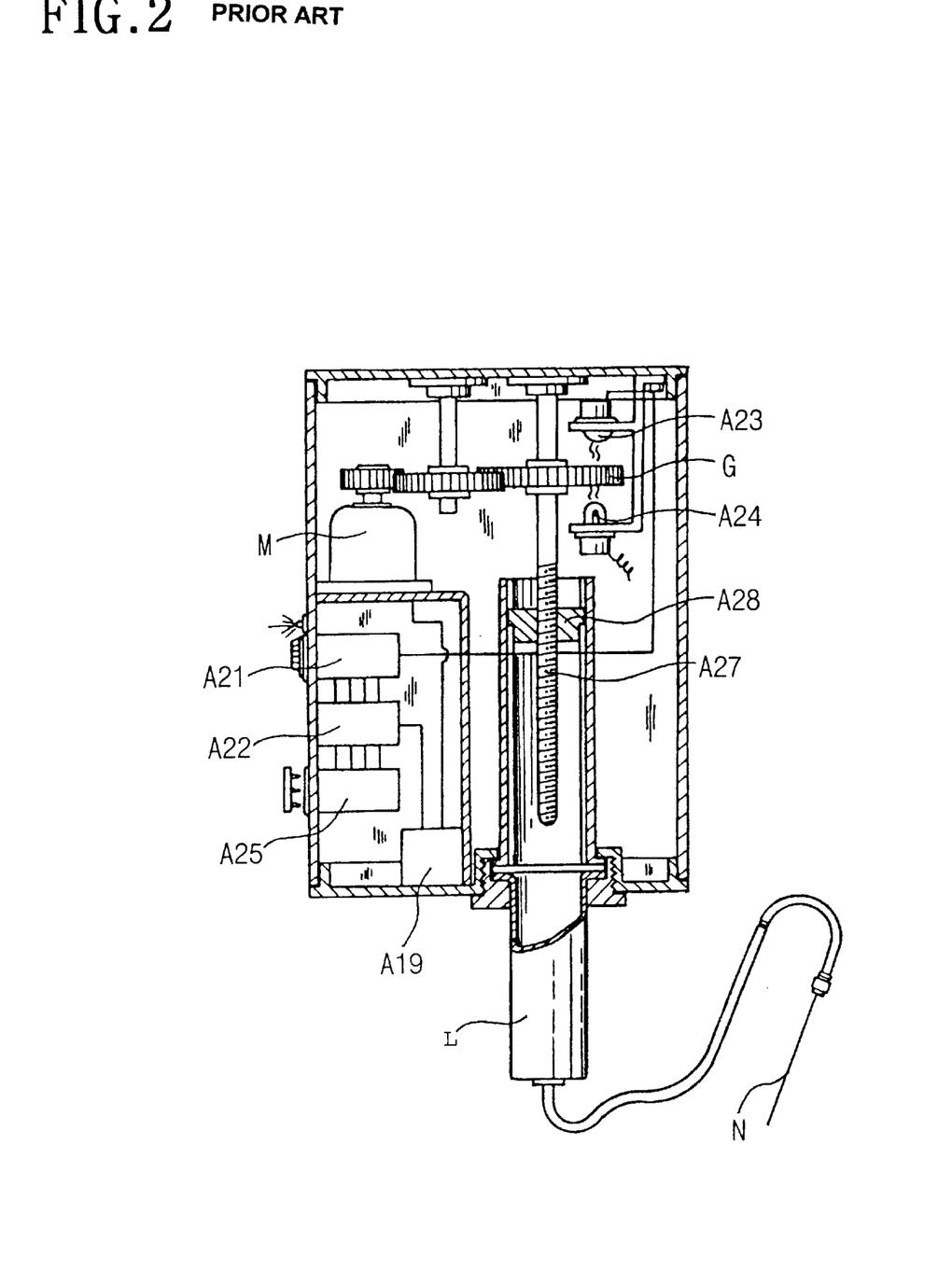
FIG. 2 is a cross-sectional view illustrating a structure of the automatic syringe device shown in FIG. 1.
Figure 3:
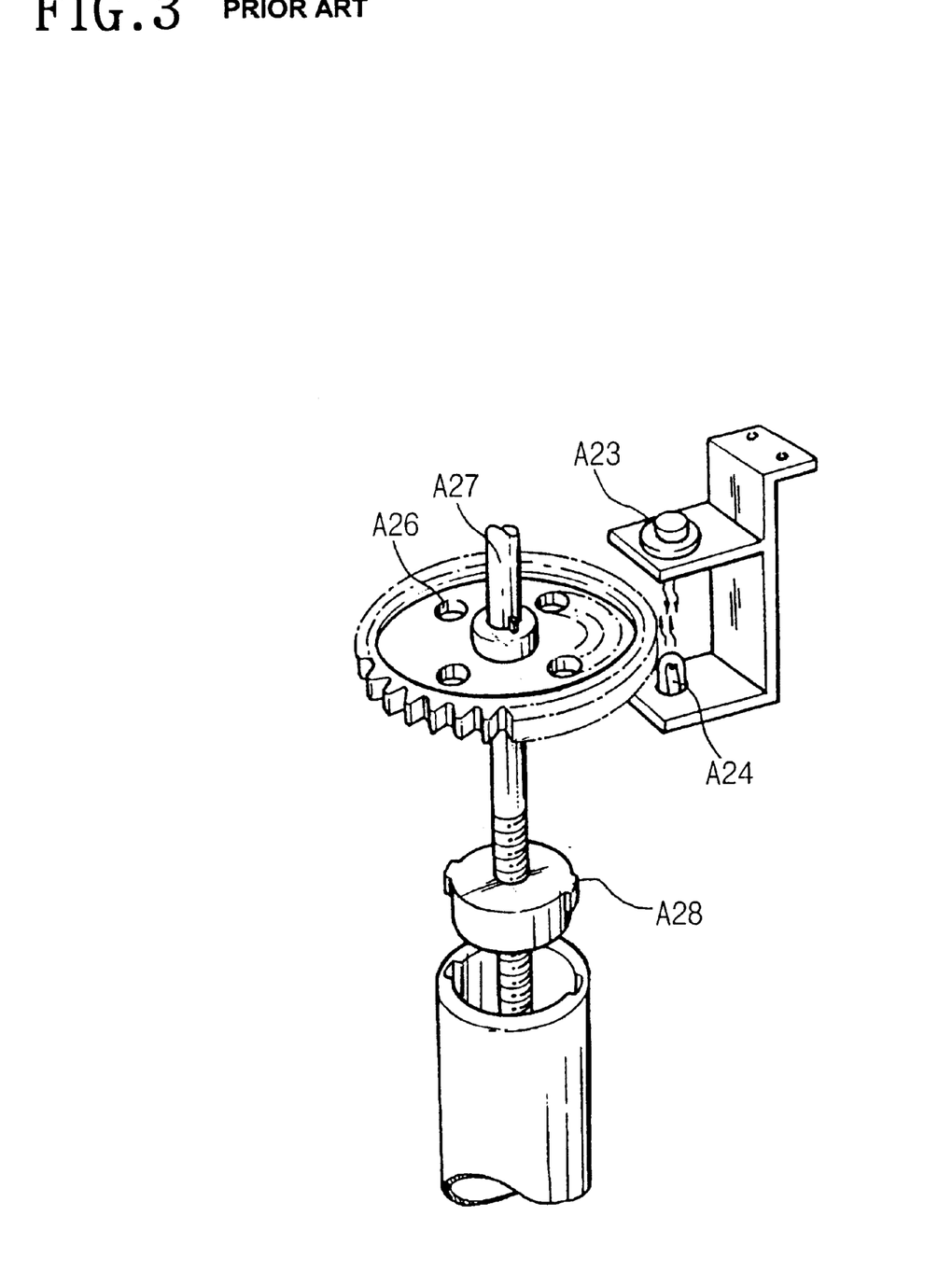
FIG. 3 is a perspective view illustrating the installation of a photo sensor in the automatic syringe device shown in FIG. 1.

Automatic syringe devices, which enable an injection of liquid medicine for a prolonged time, are well known. Typically, known automatic syringe devices have a configuration in which a push means for pushing a syringe piston is coupled to a housing receiving an injection syringe. For example, such automatic syringe devices are disclosed in Japanese Utility Model Laid-open Publication No. Sho. 52-3292 and U.S. Pat. No. 4,417,889. The syringe device disclosed in Japanese Utility Model Laid-open Publication No. Sho. 52-3292 has inconvenience in carrying it because it has an injector mounted outside a basic case, thereby requiring a double case structure. In order to solve such a disadvantage, an automatic syringe device requiring no double case structure has been proposed, as in the above mentioned U.S. Pat. No. 4,417,889. FIGS. 1 and 2 illustrate a control circuit and a structure of the automatic syringe device disclosed in U.S. Pat. No. 4,417,889, respectively. Referring to FIG. 1, the output of an oscillator A1 is coupled to a timer A2 which is, in turn, coupled at its output to a digital comparator A3. The digital comparator A3 also receives an output from a fixed number switch A4. The output of the digital comparator A3 is connected to a counter A6 and an R/S flip-flop A9. Another oscillator A5 is also provided which has an output coupled to counters A6 and A13, and AND gates A10 and A11. The flip-flop A9 is reset by an output from a digital comparator A7. Another R/S flip-flop A16 is also provided which is reset by an output from a digital comparator A14 coupled to the counter A13. A control unit A17 is also coupled to the counter A13. The control unit A17 serves to activate the counter A13 in accordance with an operation of a manual infusion switch A12. The control unit A17 applies its output to the counters A13 and A16. The output from the control unit A17 is also sent to a counter A21. The output of the counter A21 is coupled to a digital comparator A22 which is, in turn, coupled to a step motor driver A19 for driving a step motor A20. The output of the flip-flop A16 is coupled to one input of the AND gate A11, which is also coupled at the other input thereof to the oscillator A5. The output of the AND gate A11 is coupled to one input of an OR gate A18. Fixed number switches A15 and A25 are connected to the digital comparators A14 and A22, respectively. Each of the fixed number switches A4, A8, A15, and A25 has five protruding insert bars and serves to provide a reference value for an associated one of the digital comparators A3, A7, A14, and A22. A light source A24 and a photo sensor A23 are coupled to the counter A21 in order to provide sensing results thereof to the counter A21, respectively. Referring to FIGS. 2 and 3, the arrangements of the light source A24 and photo sensor A23 are illustrated. As shown in FIGS. 2 and 3, the light source A24 and photo sensor A23 are arranged in such a fashion that they face each other while being vertically spaced from each other. A gear plate, which is included in a gear mechanism G, is interposed between the light source A24 and photo sensor A23. The gear plate has a plurality of through holes A26 uniformly spaced from one another in a circumferential direction, as shown in FIG. 3. The gear plate is fixedly fitted around a gear shaft A27 having a screw portion. A piston plate A28 is threadedly coupled to the gear shaft A27 in the form of a nut in such a fashion that it slides along the screw portion of the gear shaft A27 when the gear shaft A27 rotates. The rotation of the gear shaft A is carried out by a drive force from the motor A20 transmitted via the gear mechanism G. The driving of a motor M (corresponding to the motor A20 in FIG. 1) is controlled by the operations of the counter A21, digital comparator A22, switch A25, and motor drive A19. The above mentioned elements of the syringe device are received in a housing, as shown in FIG. 2. In particular, the light source A24 and photo sensor A23 are fixedly mounted at an upper portion of the housing by means of a bracket fixed to the housing. In this syringe device, a liquid medicine, such as insulin, contained in a syringe I is outwardly injected through an injection needle N connected to the syringe I, by a sliding movement of the piston plate A28. In such a syringe device, however, the housing and syringe I thereof are exposed to ambient air. As a result, moisture and water are likely to penetrate into the syringe device. For this reason, there is inconvenience in that if the user desires to take a shower while the syringe is in place, then the housing should be contained in a separate sealing case.

Figure 4:
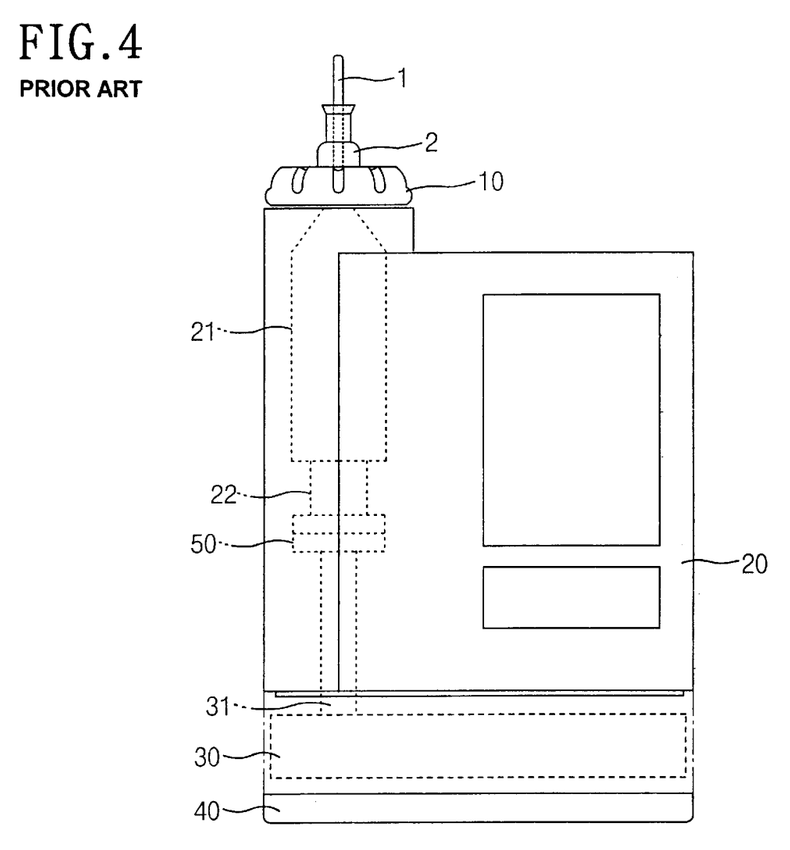
FIG. 4 is a front view illustrating another conventional automatic syringe device.

In order to solve such a problem, a sealable syringe device has been proposed by the applicant. Such a sealable syringe device is illustrated in FIG. 4 which is a front view. Referring to FIG. 4, the syringe device includes a cover 10 sealably coupled to the upper end of a housing 20, and a bottom cover 40 sealably coupled to the lower end of the housing 20. A connector 2, to which a feeding tube 1 is integrally connected, is threadedly coupled to the cover 10. The connector 2 communicates with a syringe 21 received in the housing 20. A piston 22 is slidably fitted in the syringe 21. A liquid medicine to be injected is contained in the syringe 21. A power transmission means 30 is mounted on the bottom surface of the housing 20. The power transmission means 30 has a rotating shaft 31 to which a disc type push means 50 is threadedly coupled. The disc type push means 50 moves vertically by a rotation of the rotating shaft 31, thereby vertically moving the piston 22.

Figure 5:
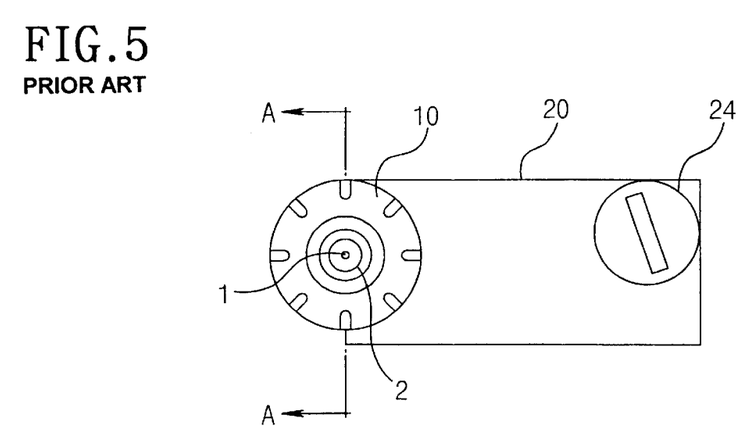
FIG. 5 is a plan view of FIG. 4.

Referring to FIG. 5, which is a plan view of FIG. 4, the cover 10, to which the connector 2 connected with the feeding tube 1 is connected, is arranged on the left portion of the upper surface of the housing 20. A battery cover 24 is arranged on the right portion of the upper surface of the housing 20.

Figure 6:
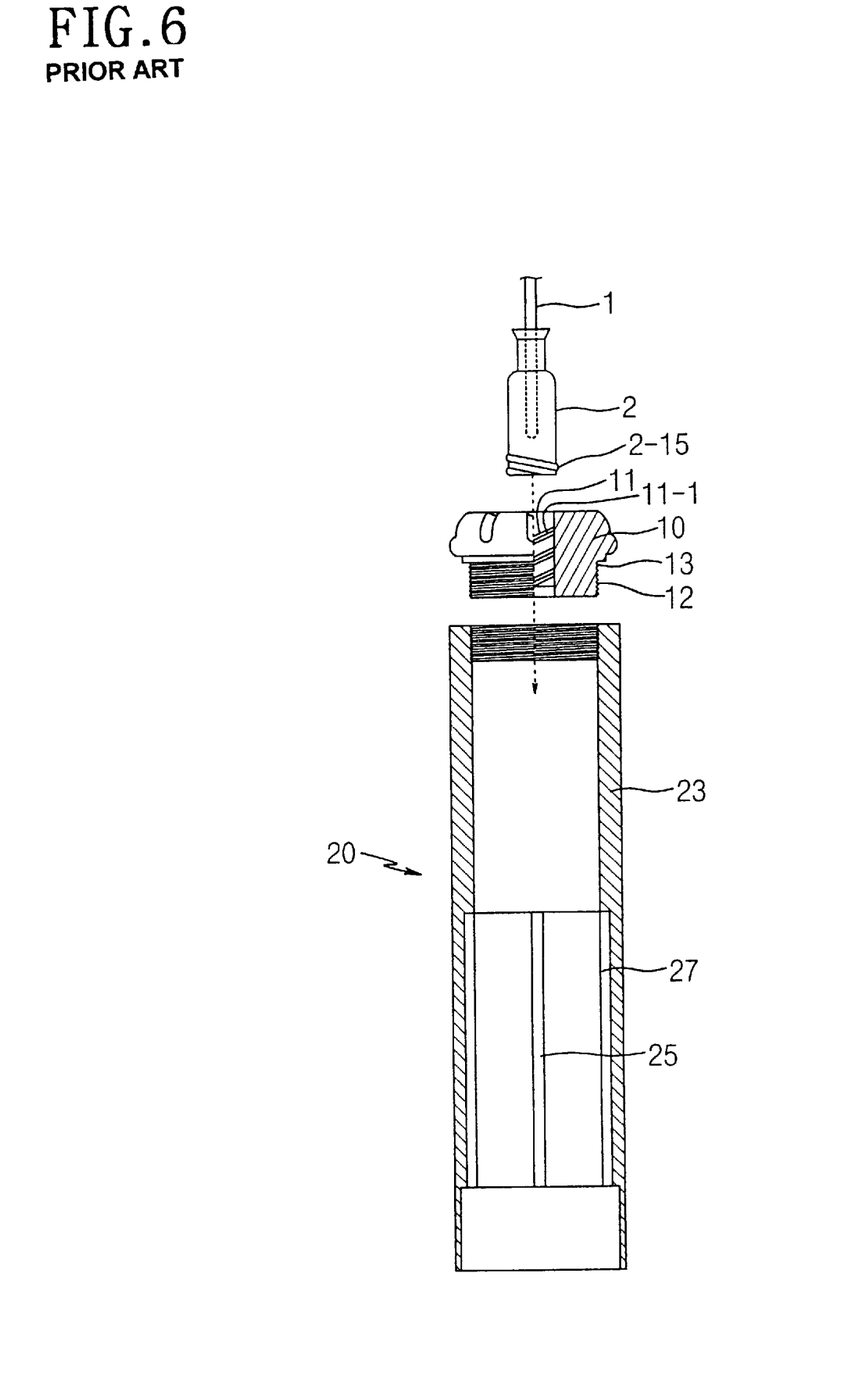
FIG. 6 is an exploded cross-sectional view taken along the line A—A of FIG. 2.

FIG. 6 is a cross-sectional view taken along the line A—A of FIG. 5. As shown in FIG. 6, the cover 10 is centrally provided with a threaded hole 11 in which the connector 2 is threadedly fitted at its lower end. The threaded hole 11 has threads 11-1. The connector 2 is formed, at its lower end, with threads 2-15 to be threadedly coupled with the threads 11-1 of the threaded hole 11. The cover 10 is also provided at its lower end with a bolt portion 12 threadedly fitted in the upper end of the housing 20. A packing 13 is fitted around the bolt portion 12 of the cover 10 between the lower end of the cover 10 and the upper end of the housing 20. A syringe receiving chamber 23 is defined in the interior of the housing 20. The push means 50 is fitted in the lower end of the housing 20 in such a fashion that it slides vertically in the housing 20. The housing 20 is also formed at its inner surface with a vertical push means guide groove 25 adapted to guide a vertical movement of the push means 50 and vertical piston guide grooves 27 adapted to guide a vertical movement of the piston 22.

Figure 7:
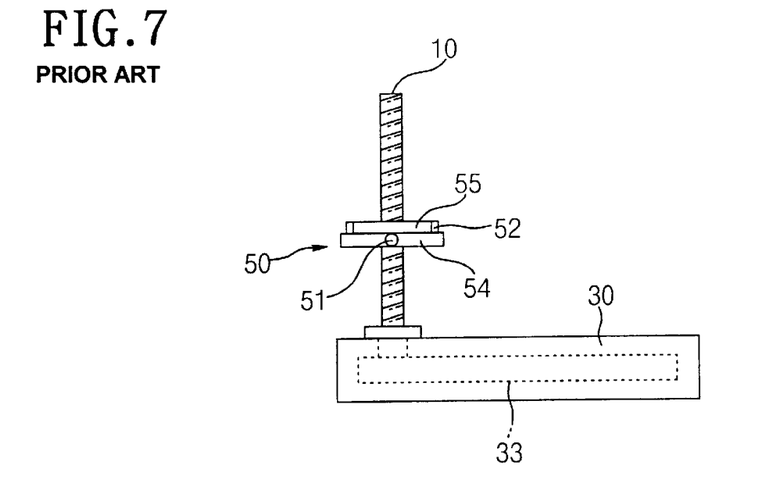
FIG. 7 is a front view illustrating a conventional power transmission means.
Figure 8:
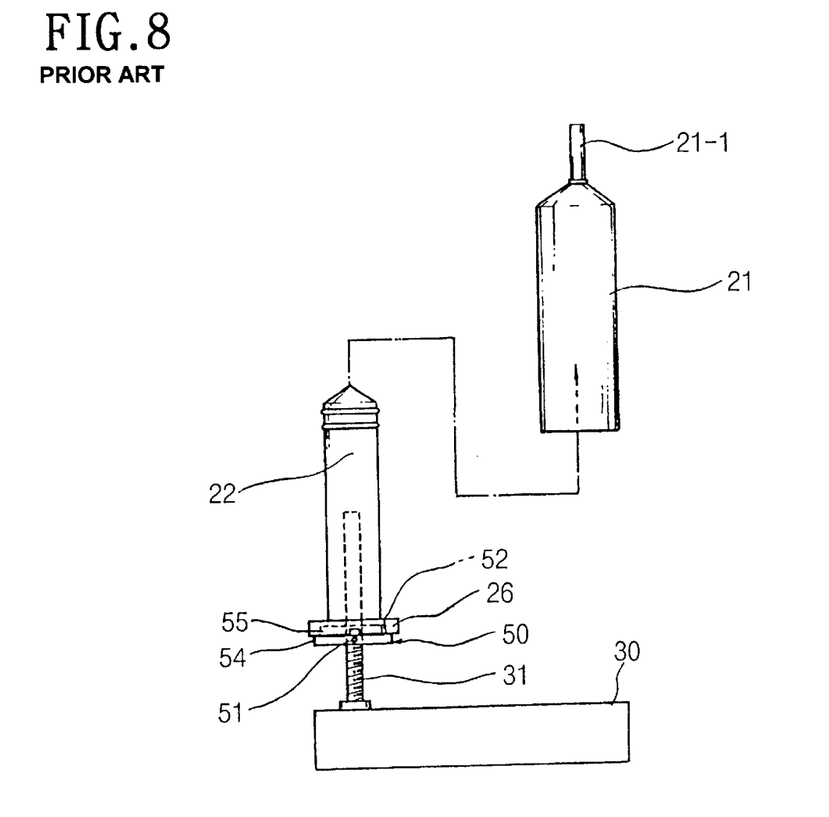
FIG. 8 is an exploded view illustrating a conventional push means.

FIG. 7 shows a detailed configuration of the power transmission means 30 mounted on the bottom surface of the housing 20 and a detailed configuration of the push means 50 threadedly coupled to the rotating shaft 31 of the power transmission means 30. As shown in FIG. 7, the push means 50 includes a lower disc 54 threadedly coupled to the rotating shaft 31 in such a fashion that it slides vertically along the rotating shaft 31. The lower disc 54 is provided at its periphery with a guide protrusion 51 engaged in the guide groove 25 of the housing 20 and adapted to guide the vertical movement of the lower disc 54. The push means 50 also includes an upper disc 55 integrally formed with the lower disc 54. The upper disc 55 is provided at its periphery with an engagement means 52. The upper disc 55 is fitted in a sleeve plate 26 (FIG. 8) fixed to the lower end of the piston 22 in such a manner that its engagement means 52 engages with a mating engagement means formed on the inner peripheral surface of the sleeve plate 26. The sleeve plate 26 is also provided at its outer peripheral surface with protrusions engaging with the guide grooves 27 respectively. The power transmission means 30 includes a reduction mechanism 33 for transmitting the rotating force of a motor (not shown) to the rotating shaft 31 in a speed-reduced manner.

In order to use the syringe device having the above mentioned configuration, the piston 22, which is in a state separated from the housing 20, is first fitted in the syringe 21, which is also in a state separated from the housing 20, in such a manner that it is completely inserted into the syringe 21. In this state, a disposable injection needle (not shown) is fitted onto the tip 21-1 of the syringe 21. Thereafter, the injection needle is penetrated into the interior of a phial through the plug of the phial. In this state, the piston 22 is pulled to suck a liquid medicine (for example, insulin) contained in the phial into the syringe 21.

The piston 22, which is in a state fitted in the syringe 21 containing the liquid medicine, is then inserted into the syringe receiving chamber 23 of the housing 20 in such a manner that it is seated on the push means 50. Subsequently, the cover 10 is threadedly coupled to the upper end of the syringe receiving chamber 23. The connector 2 is then threadedly fastened to the cover 10. As the connector 2 is threadedly fastened to the cover 10, it is fitted onto the syringe tip 21-1. Thus, the syringe 21 is maintained in a sealed state in the housing 20. When the motor (not shown) is operated under the above condition, the push means 50 moves upwardly, thereby upwardly pushing the piston 22. As a result, the liquid medicine contained in the syringe 21 is outwardly injected from the syringe 21. At this time, the upward movement of the push means 50 is accurately carried out because its guide protrusion 51 engages with the guide groove 25. Since respective protrusions of the sleeve plate 26 slide along the piston guide grooves 27 shown in FIG. 6, the upward movement of the piston 22 is also accurately carried out.

Figure 9:
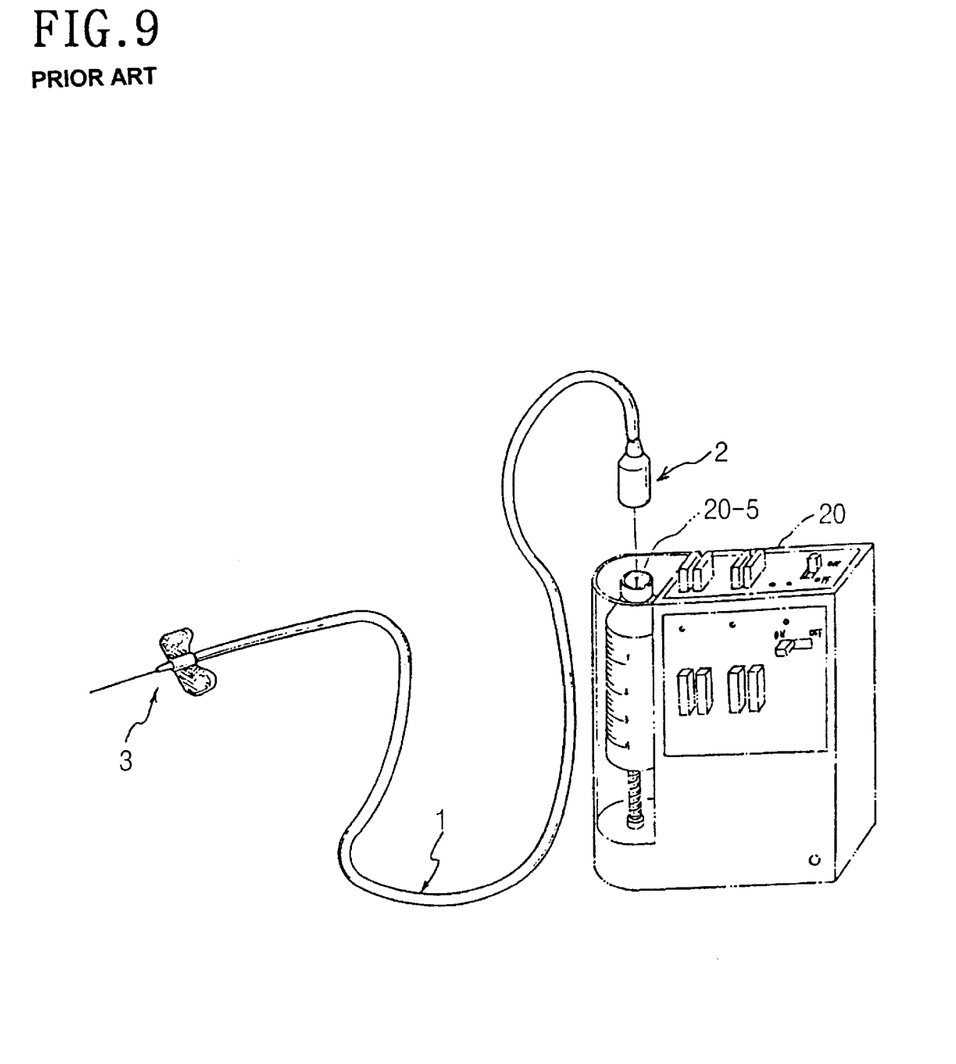
FIG. 9 is a perspective view illustrating an example of a conventional injection needle unit used for portable automatic syringe devices.

Meanwhile, FIG. 9 illustrates an example of a conventional injection needle unit used for portable automatic syringe devices enabling a prolonged injection of a liquid medicine. As shown in FIG. 9, the injection needle unit includes a feeding tube 1, a "-" shaped straight injection needle member (called a "straight butterfly-shaped injection needle") 3 connected to one end of the feeding tube 1, and a connector 2 connected to a connector portion 20-5 of the housing 20.

In order to use such an injection needle unit, the user himself angularly penetrates the straight butterfly-shaped injection needle member 3 into the subcutaneous tissue while observing the penetration of the injection needle member 3 with the naked eye. The reason why the user observes the penetration of the injection needle member 3 with the naked eye is because the injection needle member 3 has a straight shape. However, such an observation is very uncomfortable. The straight butterfly-shaped injection needle member 3 is also likely to move in the subcutaneous tissue of the user because it penetrates the subcutaneous tissue of the user at an angle. In this case, the subcutaneous tissue may be damaged. In severe cases, blood may flow out of the subcutaneous tissue. The user may also feel a severe pain.

As mentioned above, the conventional injection needle unit has a drawback in that it is difficult to smoothly inject insulin because the injection needle member 3, which penetrates the subcutaneous tissue of the user at an angle, may be easily blocked at its tip by the subcutaneous tissue. To this end, the feeding tube of such a conventional injection needle unit inevitably has an increased diameter. However, such a feeding tube having an increased diameter results in a possibility of an excessive insulin injection. In addition, this may result in wastage of expensive insulin. For instance, where it is desired to inject insulin into the user using an automatic syringe device equipped with the above mentioned injection needle unit, it is necessary to completely vent air existing in the feeding tube 1 and injection needle member 3 before penetrating the injection needle member 3 into the subcutaneous tissue of the user. To this end, insulin, which is contained in the syringe device, is outwardly discharged through the feeding tube 1 and injection needle member 3, thereby venting air. In this case, a large amount of insulin is wasted where the conventional injection needle unit having the diameter-increased feeding tube is used.

Figure 10:
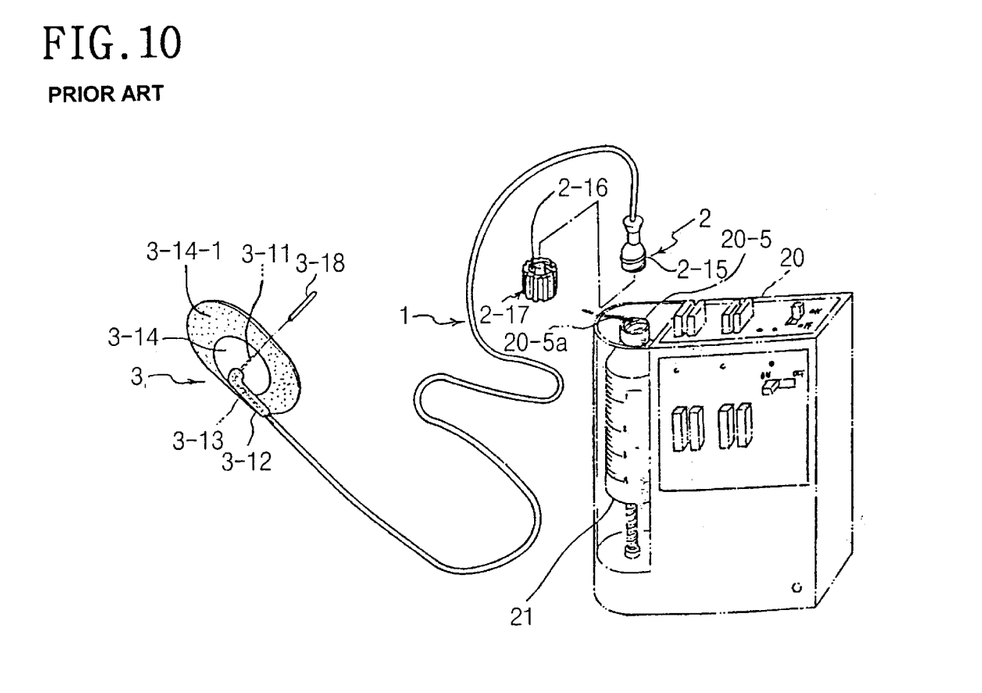
FIG. 10 is a perspective view illustrating another conventional injection needle unit.
Figure 11:
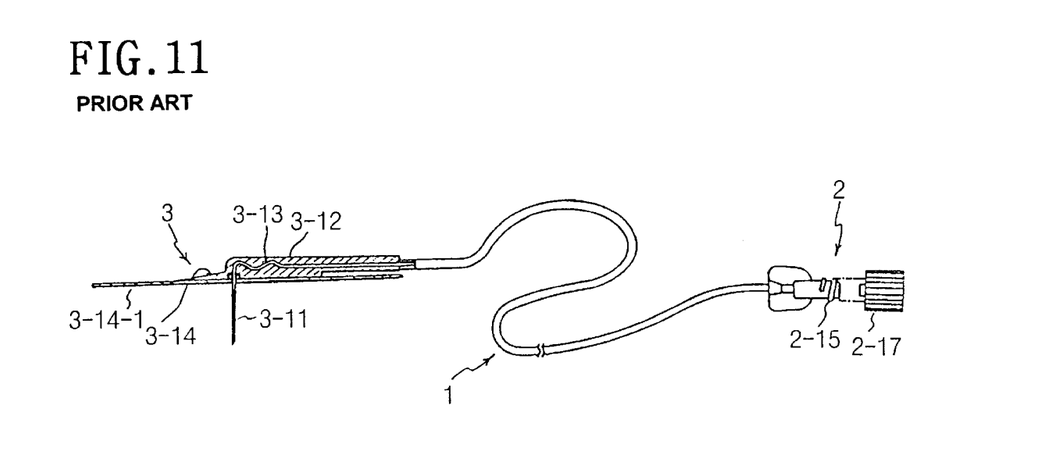
FIG. 11 is a partially broken plan view illustrating the injection needle unit of FIG. 10.

In order to solve this problem, an injection needle unit has been proposed which has an L-shaped injection needle. Such an injection needle unit is illustrated in FIGS. 10 and 11, respectively. As shown in FIGS. 10 and 11, the injection needle unit includes a feeding tube 1, an injection needle member 3 connected to one end of the feeding tube 1, and a connector 2 connected to the other end of the feeding tube 1.

Figure 12:
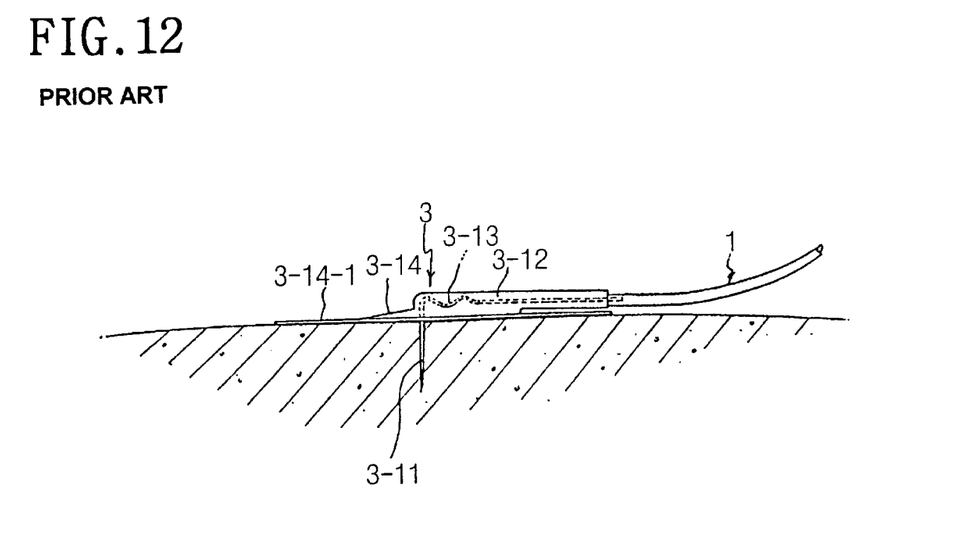
FIG. 12 is an enlarged view illustrating a using condition of the injection needle unit of FIG. 10.
Figure 13:
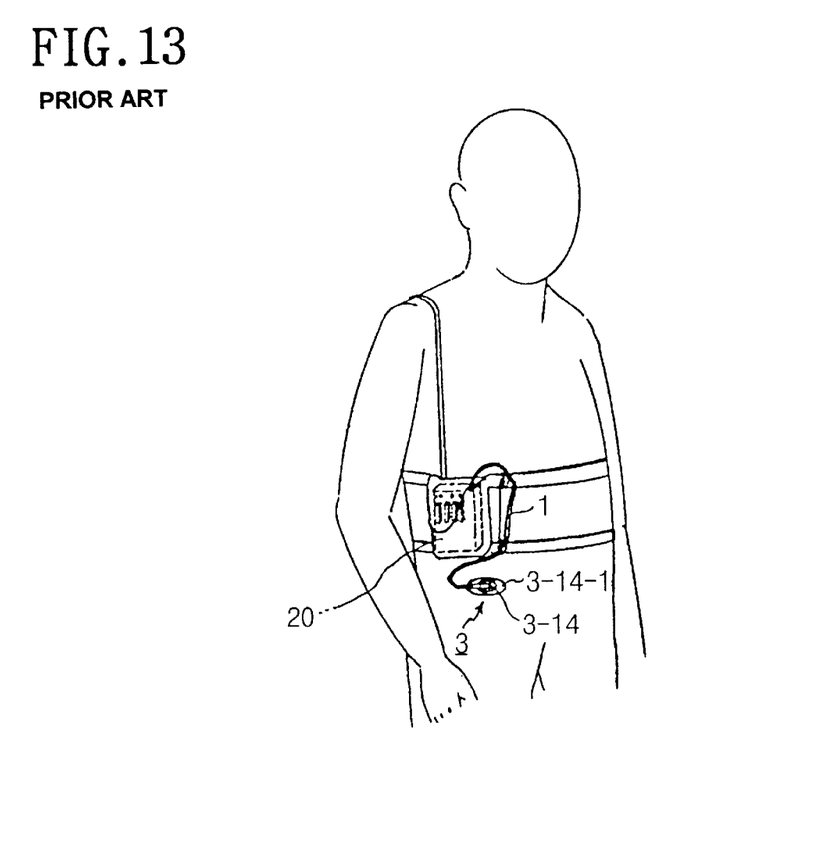
FIG. 13 is a perspective view illustrating a using condition of the injection needle unit of FIG. 10.

In the case of the injection needle unit shown in FIGS. 10 and 11, the injection needle member 3 has an injection needle 3-11 having an L-shaped structure shown in FIG. 12. This injection needle 3-11 has a first portion, namely, a horizontal portion, fitted in a connecting rib 3-12 integrally formed with one end of the feeding tube 1, and a second portion, namely, a vertical portion, provided with a needle tip. The injection needle 3-11 is provided with a curved portion 3-13 at its horizontal portion fitted in the connecting rib 3-12, as shown in FIG. 11. A depressing member 3-14 is integrally formed with the connecting rib 3-12 in such a fashion that the injection needle 3-11 protrudes perpendicularly from the depressing member 3-14. The depressing member 3-14 is depressed against the skin of the user upon penetrating the injection needle member 3 into the subcutaneous tissue. A bacterial infection prevention member 3-14-1, which is made of a sterile nonwoven fabric, is attached to the surface of the depressing member 3-14 which comes into contact with the skin of the user upon penetrating the injection needle unit 3 into the subcutaneous tissue. The connector 2, which is connected to the other end of the feeding tube 1, has a male thread 2-15. The connector 2 is protected by a protection cap 2-17 which has a female thread 2-16 threadedly coupled to the male thread 2-15 of the connector 2. In use, the connector 2 is threadedly coupled to a connector portion 20-5 of a housing 20 included in an automatic insulin syringe device. The connector portion 20-5 of the housing 20 has a female thread 20-5a threadedly coupled to the male thread 2-15 of the connector 2. In FIG. 10, the reference numeral "3–18" denotes a needle protection cap.

Where it is desired to inject insulin contained in the automatic insulin syringe device using the above mentioned injection needle unit, the protection cap 2-17 is first separated from the connector 2, which is, in turn, threadedly coupled to the connector portion 20-5 of the housing 20. Thereafter, the needle protection cap 3-18 is separated from the injection needle 3-11. The user then penetrates the injection needle 3-11 into the subcutaneous tissue while depressing the depressing member 3-14 against the skin by hand. At this time, the injection needle 3-11 penetrates vertically into the subcutaneous tissue of the user because it has an "L" shape. Accordingly, the user can carry out the penetration of the injection needle 3-11 instantaneously without any observation with the naked eye. Therefore, the user feels little pain upon penetrating the injection-needle 3-11 into the subcutaneous tissue. By virtue of such a configuration of the injection needle unit 3, the automatic insulin syringe device can be conveniently used, as shown in FIG. 13. Since the injection needle 3-11 penetrates vertically into the subcutaneous tissue of the user by virtue of its "L" shape, there is no phenomenon that the injection needle 3-11 is blocked at its tip by the subcutaneous tissue of the user. Thus, the injection of insulin is smoothly carried out. Accordingly, the feeding tube can have a reduced diameter and an increased length. Since the feeding tube 1 has a reduced diameter, it is possible to minimize the wastage of insulin occurring upon venting air existing in the feeding tube 1 and injection needle 3-11 and to reduce the manufacturing costs. Since the feeding tube 1 also has an increased length, it is possible to extend the range of the applied positions of the injection needle 3-11 on the body of the user. Accordingly, it is possible to achieve convenience in use. Since the bacterial infection prevention member 3-14-1, which is made of a sterile nonwoven fabric, is attached to the depressing member 3-14, it is possible to prevent the depressing member 3-14 from coming into direct contact with the skin of the user upon penetrating the injection needle unit 3 into the subcutaneous tissue. Accordingly, it is possible to prevent the user from being infected. Since the injection needle 3-11 penetrates vertically into the subcutaneous tissue of the user by virtue of its "L" shape, as mentioned above, it hardly moves in the subcutaneous tissue, even when an external force is applied thereto. Accordingly, there is no damage of the subcutaneous tissue. Of course, there is no phenomenon that the blood flows out of the subcutaneous tissue. The user also does not feel any pain.

However, since the injection needle used in the above mentioned injection needle unit is configured to penetrate vertically into the subcutaneous tissue of the user's abdomen or other portion, it is necessary to carry out the penetration procedure every time the injection needle is replaced by a new one. Furthermore, where it is desired to inject liquid medicine, other than the liquid medicine contained in the syringe device, into the user, it is necessary to use a separate syringe device containing the other liquid medicine.

SUMMARY OF THE INVENTION

Therefore, the present invention has been made in view of the above mentioned problems, and an object of the invention is to provide an injection needle unit for a portable automatic syringe device which includes a feeding tube divided into first and second tube portions respectively connected to a syringe pump connector and an injection needle member, first and second head units respectively coupled to facing ends of the first and second tube portions, and a coupling ring for separably coupling the first and second head units to each other, thereby being capable of achieving easy separation and coupling of the injection needle member from a syringe pump, so that when it is desired to inject liquid medicine, other than the liquid medicine contained in the syringe device, into the user, this can be achieved by injecting the other liquid medicine into the sealing member of the second head unit without directly injecting the other liquid medicine into the user.

In accordance with the present invention, this object is accomplished by providing an injection needle unit for a portable automatic syringe device adapted to perform an injection of liquid medicine into the body of a user for a prolonged time, comprising a connector coupled to an insulin pump included in the syringe device to connect the injection needle unit to the insulin pump, and an injection needle member, the injection needle unit further comprising: a feeding tube coupled with the connector and the injection needle member at opposite ends thereof, respectively, to connect the injection needle member to the insulin pump, the feeding tube being divided into a first tube portion connected to the connector and a second tube portion connected to the injection needle member; a first head unit mounted to an end of the first tube portion opposite to the connector while communicating with the first tube portion, the first head unit including a cylindrical body defining a recess therein and having a cylindrical wall divided into a plurality of wall portions by longitudinal guide slits, and a connecting needle mounted to the cylindrical body while communicating with the first tube portion at one end thereof and extending into the recess at the other end thereof; a second head unit mounted to an end of the second tube portion opposite to the injection needle member while communicating with the second tube portion, the second head unit including a sealing member received in an end portion of the second head unit opposite to the second tube portion; and a coupling ring adapted to separably couple the first and second head units to each other and provided at an inner surface thereof with guide protrusions adapted to slide along the guide slits.

BRIEF DESCRIPTION OF THE DRAWINGS

Other objects and aspects of the invention will become apparent from the following description of embodiments with reference to the accompanying drawings in which.

DESCRIPTION OF THE PREFERRED EMBODIMENTS

Now, the present invention will be described in detail with reference to the annexed drawings.

Figure 14:
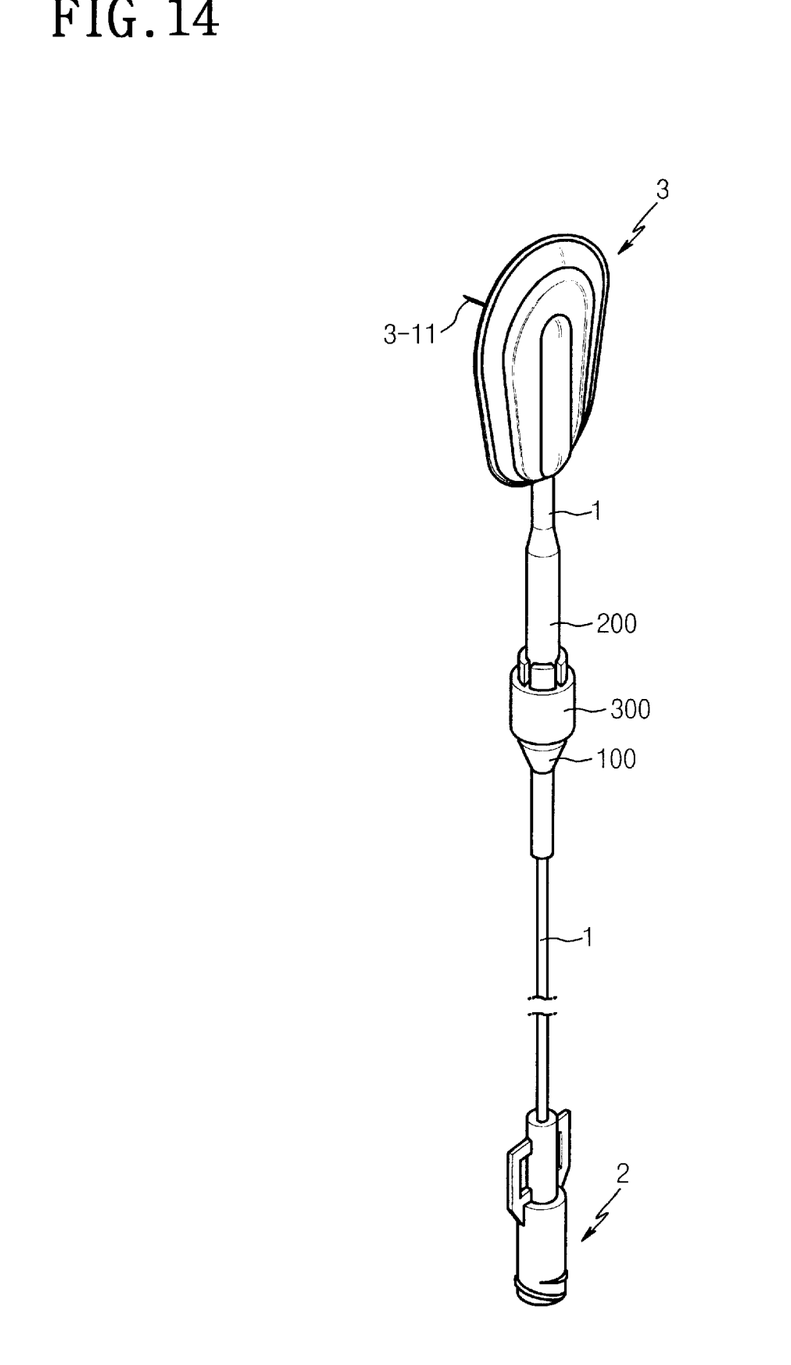
FIG. 14 is a perspective view illustrating an injection needle unit for a portable automatic syringe device according to the present invention.
Figure 15:
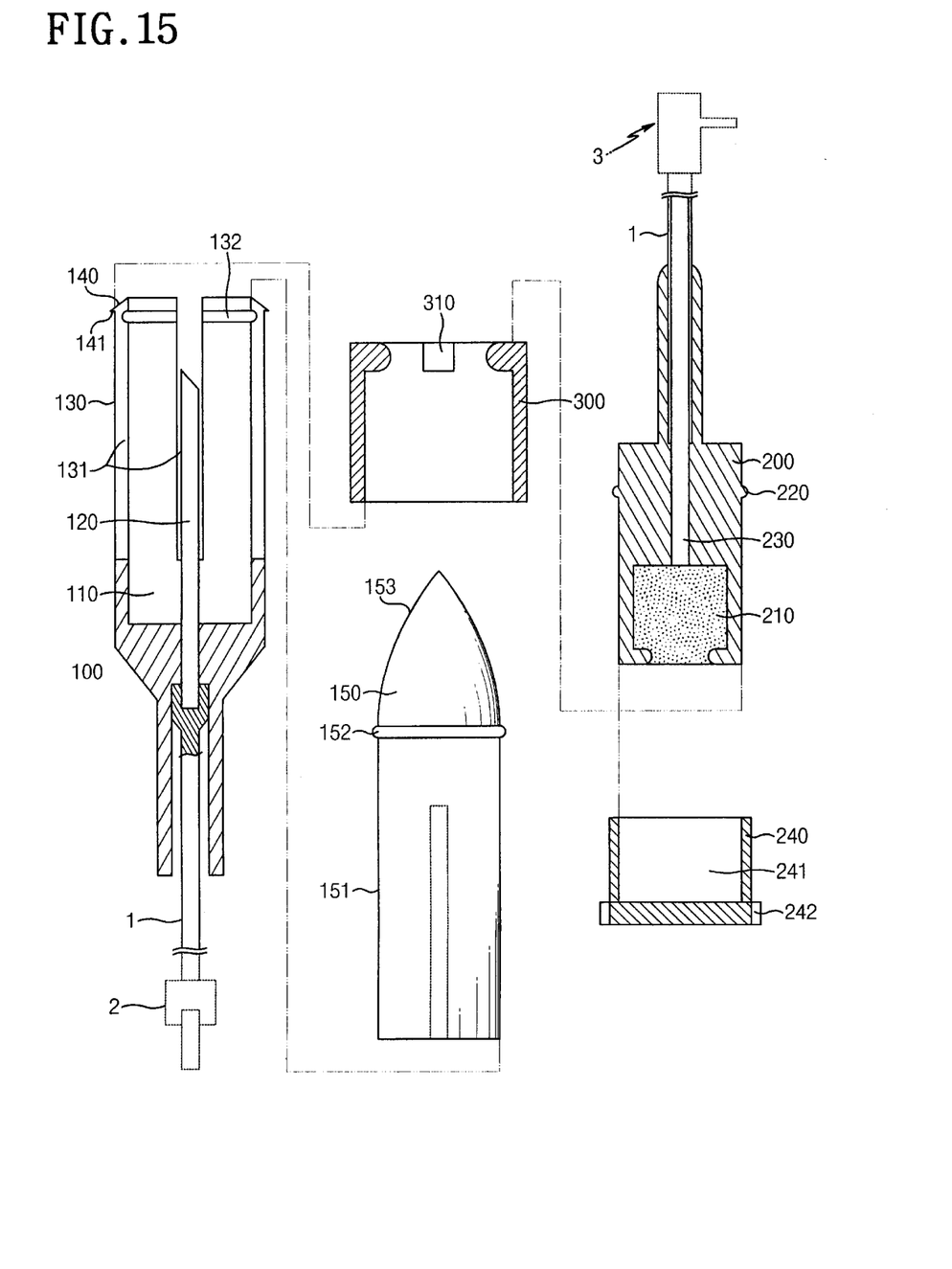
FIG. 15 is a partially broken exploded enlarged sectional view illustrating the injection needle unit according to the present invention.
Figure 16:
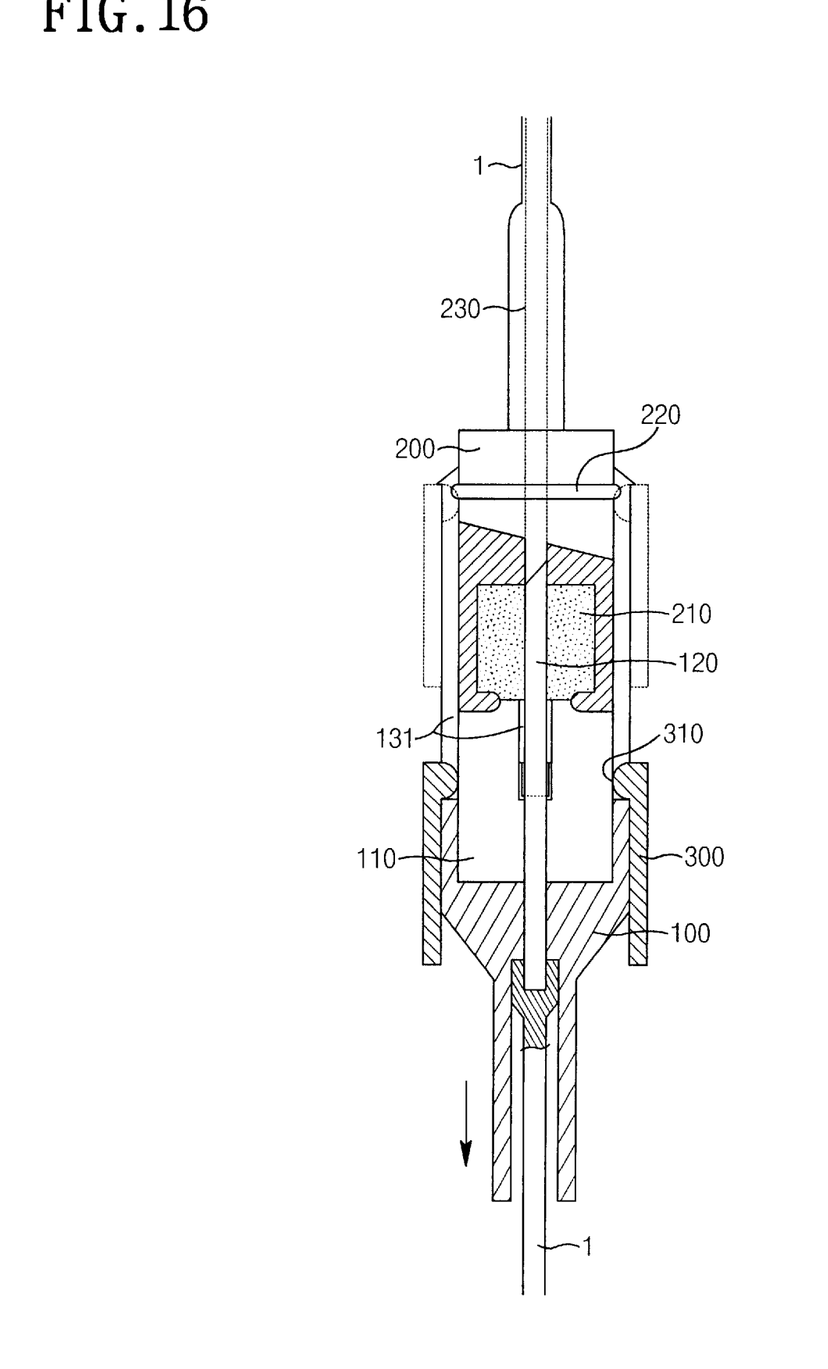
FIG. 16 is a partially broken assembled enlarged sectional view illustrating the injection needle unit according to the present invention.

FIG. 14 is a perspective view illustrating an injection needle unit for a portable automatic syringe device according to the present invention. FIG. 15 is a partially broken exploded enlarged sectional view illustrating the injection needle unit according to the present invention. FIG. 16 is a partially broken assembled enlarged sectional view illustrating the injection needle unit according to the present invention. The injection needle unit of the present invention is applied to a portable automatic syringe device adapted to perform an injection of liquid medicine into the body of the user for a prolonged time. The injection needle unit includes a feeding tube 1, a connector 2 coupled to an insulin pump included in the syringe device to connect one end of the feeding tube 1 to the insulin pump, and an injection needle member 3 connected to the other end of the feeding tube 1.

As shown in FIG. 14, the feeding tube 1 is divided into two tube portions, that is, a first tube portion connected to the connector 2 and a second tube portion connected to the injection needle member 3. The injection needle unit also includes a first head unit 100 mounted to an end of the first tube portion of the feeding tube 1 opposite to the connector 2 while communicating with the first tube portion. The first head unit 100 has a cylindrical body defining a recess 110 therein. The injection needle unit further includes a second head unit 200 mounted to an end of the second tube portion of the feeding tube 1 opposite to the injection needle member 3 while communicating with the second tube portion. As shown in FIG. 15, a sealing member 210 is received in an end portion of the second head unit 200 opposite to the second tube portion of the feeding tube 1. Also, the injection needle unit includes a coupling ring 300 for separably coupling the first and second head units 100 and 200 to each other.

As shown in FIG. 15, the first head unit 100 includes a connecting needle 120 centrally mounted to the cylindrical body of the first head unit 100 while communicating with the first tube portion of the feeding tube 1 at one end thereof and extending into the recess 110 at the other end thereof. The cylindrical body of the first head unit 100 has a cylindrical wall 130 divided into a plurality of wall portions by longitudinal guide slits 131. The coupling ring 300 is provided at its inner surface with guide protrusions adapted to slide along the guide slits 131.

An annular hook 140 is formed at an end of the cylindrical wall 130 of the first head unit 100 opposite to the first tube portion of the feeding tube 1. The annular hook 140 serves to prevent the coupling ring 300 from being separated from the first head unit 100.

Adjacent to the annular hook 140, an annular groove 132 is formed at the inner surface of the cylindrical wall 130. The second head unit 200 is provided at its outer surface with an annular protrusion 220 to be engaged with the annular groove 132.

The cylindrical wall 130, which is divided into a plurality of wall portions by the guide slits 131, is structured to have a larger diameter at the bottom of the recess 110 than at the top of the recess 110.

As mentioned above, the first head unit 110 is coupled to the first tube portion of the feeding tube 1 at one end thereof while having the cylindrical wall 130 defined with the recess 110 at the other end thereof. The longitudinal guide slits 131 formed at the cylindrical wall 130 serve to guide the guide protrusions 310 of the coupling ring 300. The end of the feeding tube 1 connected to the first head unit 110 is connected with one end of the connecting needle 120. The other end of the connecting needle 120 is protruded into the recess 110.

The second head unit 200 is centrally provided with a connecting hole 230 which is connected with the second tube portion of the feeding tube 1 at one end thereof while being in contact with the sealing member 210 at the other end thereof.

The first head unit 100 also includes a head unit plug 150 made of an elastic material. The head unit plug 150 is fitted in the recess 110 when the first and second head units 100 and 200 are separated from each other, in order to prevent the connecting needle 120 from being contaminated. The head unit plug 150 includes a fitting portion 151 adapted to be fitted in the recess 110 of the first head unit 100, a stop ring 152 adapted to come into contact with the hook 140 of the first head unit 100 when the fitting portion 151 is inserted into the recess 110, thereby stopping the insertion of the fitting portion 151, and a knob 153 for allowing the user to handle the head unit plug 150 upon fitting the head unit plug 150 in the recess 110.

The second head unit 200 also includes a head unit cap 240 preferably made of an elastic material and fitted around the end of the second head unit 200, where the sealing member 210 is positioned, when the first and second head units 100 and 200 are separated from each other, in order to prevent the sealing member 210 from being contaminated. The head unit cap 240 has a fitting hole 241 for receiving the end of the second head unit 200, and protrusions 242 provided at an end of the head unit cap 240 opposite to the end of the second head unit 200 and adapted to allow the user to easily handle the head unit cap 240 when the head unit cap 240 is to be separated from the second head unit 200.

The hook 140 has an annular hooking protrusion 141 outwardly protruded from the outer surface of the cylindrical wall 130 and adapted to prevent the coupling ring 300 from being separated from the first head unit 100.

Now, the operation of the injection needle unit having the above mentioned configuration according to the present invention will be described. In order to use the injection needle unit of the present invention in a portable syringe device, for example, the syringe device s shown in FIG. 10, the syringe 21 containing a liquid medicine is first seated in the housing 20 which is, in turn, covered by the cover 10. Thereafter, the connector 2 connected to the feeding tube 1 carrying the injection needle member 3 is threadedly coupled to the cover 10. The injection needle member 3 is then penetrated into the abdomen of the user, as shown in FIG. 13, in order to use the syringe device. As mentioned above, the feeding tube 1 is divided into two tube portions, that is, the first tube portion connected to the connector 2 and the second tube portion connected to the injection needle member 3. The first and second tube portions of the feeding tube 1 are connected to each other by the first and second head units 100 and 220 coupled together by the coupling ring 300. When the coupling ring 300 is moved from its coupling state indicated by a phantom line in FIG. 16 to a state indicated by a solid line in FIG. 16, the cylindrical wall 130 of the first head unit 100 divided into a plurality of wall portions by the guide slits 131 is increased in diameter. In this state, when the user pulls the first head unit 100 in a direction opposite to the second head unit 200, that is, the direction indicated by an arrow in FIG. 16, the first head unit 100 is separated from the second head unit 200. The separated state is shown in FIG. 15. Although the coupling ring 300 is shown as being in a separated state in FIG. 15, it is practically maintained in a state in which it is coupled to the first head unit 100, when the first head unit 100 is separated from the second head unit 200. The illustration of FIG. 15 is only for an easy understanding of the configuration of the injection needle unit according to the present invention. That is, FIG. 15 illustrates the state of the injection needle unit before the coupling ring 300 is fitted around the tube wall 130 of the first head unit 100. After the separation of the first head unit 100 from the second head unit 200, the user inserts the head unit plug 150 into the recess 110 of the first head unit 100 while grasping the knob 153 of the head unit plug 150 by the fingers, so as to fit the fitting portion 151 of the head unit plug 150 in the recess 110. Thus, the connecting needle 120 is covered by the head unit plug 150, so that it is prevented from being contaminated. Also, the user fits the head unit cap 240 around the second head unit 200 so that the end of the second head unit 200 carrying the sealing member 210 is fitted in the fitting hole 241 of the head cap 240, thereby preventing the sealing member 210 from being contaminated. As the first and second head units 100 and 200 are separated from each other, the injection of the liquid medicine is temporarily stopped. If necessary, a separate liquid medicine may be injected into the feeding tube 1 via the sealing member 210 in order to inject the liquid medicine into the user. Thus, the injection needle unit of the present invention makes it possible for the syringe device to inject different liquid medicines without any separation of the needle member 3 from the user.

In order to couple again the first and second head units 100 and 200 to each other, the plug 150 and cap 240 are separated from the head units 100 and 200, respectively. Thereafter, the second head unit 200 is fitted in the recess 110 of the first head unit 100. As the second head unit 20 is inserted into the recess 110, the connecting needle 120 is penetrated into the sealing member 210, so that it communicates with the connecting hole 230 of the second head unit 200. As a result, the liquid medicine from the syringe 21 can be fed to the needle member 3 via the first and second head units 100 and 200. The annular protrusion 220 of the second head unit 200 is engaged with the annular groove 132 formed at the inner surface of the cylindrical wall 130 included in the first head unit 100. The engagement of the annular protrusion 220 and annular groove 132 is naturally achieved by a depressing force applied to the cylindrical wall 130 by the coupling ring 300 when the coupling ring 300 is longitudinally moved from the position indicated by the solid line in FIG. 16 to the position indicated by the phantom line in FIG. 16. At this time, the movement of the coupling ring 300 is guided by the guide slits 131 provided at the cylindrical wall 130 of the first head unit 100 and the guide protrusions 310 provided at the inner surface of the coupling ring 300, so that the coupling ring 300 can reliably couple the first and second head units 100 and 200 to each other.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

As apparent from the above description, the present invention provides an injection needle unit for a portable automatic syringe device which includes a feeding tube divided into first and second tube portions respectively connected to a syringe pump connector and an injection needle member, first and second head units respectively coupled to facing ends of the first and second tube portions, and a coupling ring for separably coupling the first and second head units to each other, thereby being capable of achieving easy separation and coupling of the injection needle member from a syringe pump. In order to easily achieve separation and coupling of the first and second head units, the first and second head units are provided with an annular protrusion and an annular groove to be engaged with each other, respectively. The coupling ring can move longitudinally along the outer surface of the first head unit to separably couple the first and second head units to each other. By virtue of such a configuration, the coupling state of the first and second head units can be firmly maintained using a reduced coupling force.

In accordance with the present invention, where it is desired to inject liquid medicine, other than the liquid medicine contained in the syringe device, into the user, this can be achieved by injecting the other liquid medicine into the sealing member of the second head unit without directly injecting the other liquid medicine into the user. Accordingly, there is an effect of preventing the user from feeling any pain due to the injection of liquid medicine other than the liquid medicine contained in the syringe device.

What is claimed is:

1. An injection needle unit for a portable automatic syringe device adapted to perform an injection of liquid medicine into the body of a user for a prolonged time, comprising a connector coupled to an insulin pump included in the syringe device to connect the injection needle unit to the insulin pump, and an injection needle member, the injection needle unit further comprising:

a feeding tube coupled with the connector and the injection needle member at opposite ends thereof, respectively, to connect the injection needle member to the insulin pump, the feeding tube being divided into a first tube portion connected to the connector and a second tube portion connected to the injection needle member;

a first head unit mounted to an end of the first tube portion opposite to the connector while communicating with the first tube portion, the first head unit including a cylindrical body defining a recess therein and having a cylindrical wall divided into a plurality of wall portions by longitudinal guide slits, and a connecting needle mounted to the cylindrical body while communicating with the first tube portion at one end thereof and extending into the recess at the other end thereof;

a second head unit mounted to an end of the second tube portion opposite to the injection needle member while communicating with the second tube portion, the second head unit including a sealing member received in an end portion of the second head unit opposite to the second tube portion; and a coupling ring adapted to separably couple the first and second head units to each other and provided at an inner surface thereof with guide protrusions adapted to slide along the guide slits.

2. The injection needle unit according to claim 1, wherein the first head unit further includes an annular hook formed at an end of the cylindrical wall of the first head unit opposite to the first tube portion of the feeding tube, the annular hook serving to prevent the coupling ring from being separated from the first head unit.

3. The injection needle unit according to claim 1, wherein:

the first head unit further includes an annular groove formed at an inner surface of the cylindrical wall; and the second head unit further includes an annular protrusion formed at an outer surface of the second head unit and adapted to be engaged with the annular groove.

* * * * *